United States Patent [19]

Brown

[11] Patent Number: 4,857,713

[45] Date of Patent: Aug. 15, 1989

[54] HOSPITAL ERROR AVOIDANCE SYSTEM

[76] Inventor: Jack D. Brown, Rte. 1, Box 193, Fall Branch, Tenn. 37656

[21] Appl. No.: 829,199

[22] Filed: Feb. 14, 1986

[51] Int. Cl.$^4$ .................. G06F 15/42; G06K 5/00
[52] U.S. Cl. ........................... 235/375; 235/472; 364/401; 364/413.01
[58] Field of Search ................ 235/375–377, 235/380–382, 385, 462, 494, 487, 472; 364/400, 401, 402, 413, 415

[56] References Cited

U.S. PATENT DOCUMENTS

| | | | |
|---|---|---|---|
| 3,831,006 | 8/1974 | Chaffin et al. | 235/375 |
| 3,848,112 | 11/1974 | Weichselbaum et al. | 235/375 |
| 4,164,320 | 8/1979 | Irazoqui et al. | 235/375 |
| 4,415,802 | 11/1983 | Long | 235/375 |
| 4,476,381 | 10/1984 | Rubin | 235/375 |
| 4,481,412 | 11/1984 | Fields | 235/385 |
| 4,614,366 | 9/1986 | North et al. | 235/375 |
| 4,628,193 | 12/1986 | Blum | 235/375 |
| 4,695,954 | 9/1987 | Rose et al. | 364/413 |

*Primary Examiner*—Raymond F. Cardillo
*Assistant Examiner*—Robert A. Weinhardt

[57] ABSTRACT

A Hospital Error-Limiting Program (HELP) directed primarily at reduction of hospital errors in the delivery of medications, goods, services or procedures in patient treatment without a requirement to create patient labels and with the ability to verify frequency of dosage and other treatment specifications. The invention includes a patient wrist identification band with preprinted barcode. The barcode should be selected to correspond with the standard used to barcode unit dose medications. The portable computer should be small in size and equipped with a communication link with the host computer or barcode reader. The portable computer should preferably be coupled directly to the host computer means of the hospital for data transmission by a communication link. The portable computer should be loaded with physician's orders for medications, goods, services or procedures for specific patients. Before medications, goods, services or procedures are administered to a patient, hospital personnel will scan the machine readable code on the patient's identification band, and then the machine readable code on the unit dose(s) of the medications, goods, services, or procedures will be scanned. The portable computer will compare these readings with the doctor's orders and other internal files as required and verify that the administration of the identified medications, goods, services or procedures is either correct or not correct.

1 Claim, 2 Drawing Sheets

HOSPITAL ERROR AVOIDANCE SYSTEM

BACKGROUND OF THE INVENTION

1. Field of the Invention

The present invention relates to a computer system and associated methods for limiting errors in hospitals and other medical institutions using machine-readable code on patient identification bands, medications, other goods, services, procedures, and treatments; and providing accurate, direct linkage in the computer system using existing machine codes without generating labels, and including verification of dosage rates.

2. Background Art

Several methods and systems for identification and verification of patient treatment have been used in medical institutions. However, as described below, such methods and systems have presented certain disadvantages.

For example, prior art patient identification methods and systems have identified patients with machine readable code and generated identifying labels for fixation to blood or other specimen containers, as well as performed validation procedures to confirm that a particular medication is to be administered to a patient or a particular test is to be performed on the patient. According to one method disclosed in U.S. Pat. No. 4,476,381 the identifying indicia are translucent to ultraviolet light and capable of reproducing the identifying indicia on an ultraviolet-sensitive label for use in identification of patient specimens.

A significant disadvantage of such a method is the requirement for generating and affixing of labels to link patients with prescribed materials and procedures which is an added operation subject to human error and is costly. A further disadvantage is the requirement for an apparatus to provide the ultraviolet light source used to reproduce labels used to identify specimen containers, medications, procedures, and other patient treatments. A further disadvantage is the requirement for storage of barcode information for matching the patient indicia and specimen containers, medications, procedures, and other patient treatments in computer registers and checking for identity which precludes use of existing standard barcodes on unit dose medications, specimen containers, procedures and treatments. A still further disadvantage of the method is the lack of procedures for verifying treatment prescription using computer-based comparisons of authorized and delivered medications and treatments. Moreover, no method for verification of the rate of dosage for medications is provided in the system.

Other methods used in the prior art call for identification to be attached to the wristlet worn by the patient, an example of such method being disclosed in U.S. Pat. No. 4,415,802. Such method has the disadvantage of requiring additional steps in the delivery of medications directed at error avoidance at the final point of delivery to the patient, in effect transferring the potential source of medication error in the assembly of medications from the patient location to the location where the medications are placed in a locked container for delivery to the patient. A further disadvantage is the requirement for the use of a lock container for all medication delivery and in so doing burden the operation of the hospital with additional work steps while only transferring the location of potential medication errors from the patient location to the assembly point for inclusion in the locked container.

Another example of such a method is disclosed U.S. Pat. No. 4,628,193. Such method has the disadvantage of requiring an apparatus embodying a portable microcomputer with an electrically powered hand stamp mechanism. A further disadvantage is the specification of a computer printed list for routing and scheduling patient treatments separate from, and in addition to, the portable microcomputer with the requirement that the list must be stamped by the embodied electrically powered hand stamp mechanism before treatment can continue, and further, the use of the embodied electrically powered hand stamp mechanism for test tube label printing.

SUMMARY OF THE INVENTION

The invention should be in the form of wrist identification bands with preprinted barcode. The barcode used on the wrist identification bands should be selected to correspond with the standard used to barcode the unit dose medications. The portable computer means should be small in size and equipped with a barcode reader. A hand held portable computer means such as Model PTC-701 manufactured by Telxon Corporation, or the Advanced Pocket Computer manufactured by Hand Held Products, is able to read the barcode on the patient's identification band and a variety of other standard barcode formats. The portable computer means should preferably be coupled directly to the host computer means for up-loading and down-loading data a host computer means using a communication link means. The portable computer means should be downloaded with physician's orders for medications, goods, services or procedures for specific patients.

Before medications, goods, services or procedures are administered to a patient, hospital personnel will scan the machine-readable code on the patient's identification band, and the machine-readable code on the unit dose(s) of the medications, goods, services or procedures. The portable computer means will compare these readings with the doctor's orders and other internal files as required and verify that the administration of the medications, goods, services or procedures is either correct or not correct.

The patient identification band may have a barcode label added, or may utilize an alternate machine-readable code. The scanning device may be hard-wired, connected by radio, infra-red sensor, or other communication technique to a host computer means, or a local area network, or a standalone computer means, or other computer system. A portable computer means may be totally self-contained. The patient identification band may also be used for other hospital administration purposes.

This invention will permit the combination of machine-readable identification of patients, and machine-readable identification of medications, goods, services or procedures coding with computer based physician instructions for delivery of goods, services or medical procedures including tests and medications into an automatic error avoidance system.

The machine-readable code on the patient identification band will provide additional benefits to hospital administration. The invention will permit a portable computer means to automatically record the time, date, patient identification code, and medications, goods, services or procedures delivered. These records can be loaded into the host computer means automatically to form a complete record of patient transactions for billing and other purposes.

DESCRIPTION OF THE PREFERRED EMBODIMENTS

Figure 1:
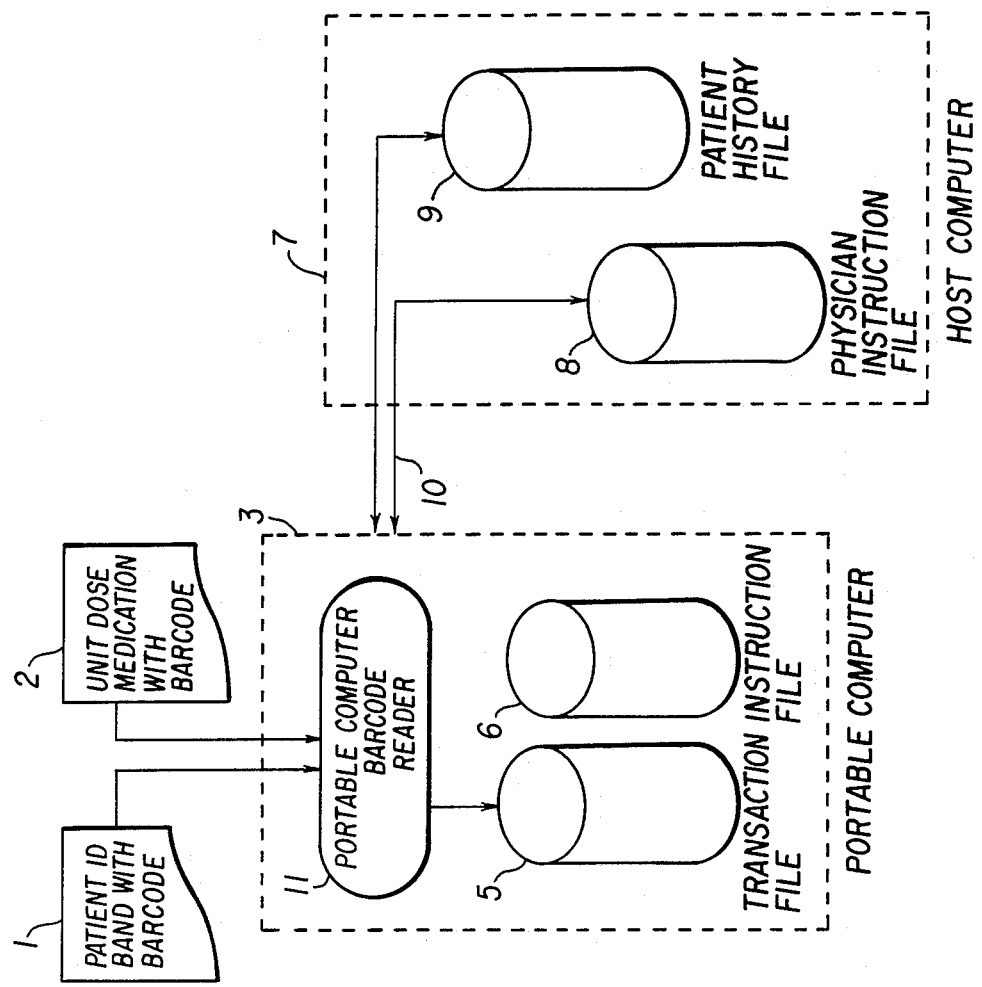
FIG. 1 is a block diagram of a system embodying the invention.

FIG. 1 shows the patient identification band with barcode 1. At the time of delivery of medication, goods, service or procedure, hospital personnel will scan the patient identification band barcode 1 to determine the patient's identity and then scan the unit dose medication, goods, service or procedure barcode 2 to identify the medication and size of dose, goods, service or procedure.

The portable computer means 3 will check its internal file of physician's instructions 6 to verify that the identified medication, goods, service or procedure 2 has been prescribed for the identified patient 1. If the medication and dosage, goods, service or procedure is correct the portable computer means will check the transaction file 5 to for the last recorded delivery of the medication, goods, service or procedure. The portable computer means 3 will calculate the time interval since the last recorded delivery of the medication, goods, service or procedure with the time interval prescribed in the physician instruction file 6. If the interval is correct the portable computer means will display the message "verified". If an error occurs in this process, an appropriate error message will be displayed by the portable computer means.

The transaction file 5 and the physician instruction file 6 are contained in the portable computer means 3. The transaction file 5 is uploaded into a host computer means 7 patient history file 9 periodically. Physician instructions contained in file 8 in the host computer means 7 are downloaded to the instruction file 6 in the portable computer means 3 before each delivery tour of medication, goods, services or procedure is begun.

When a patient is to receive a procedure (eg. X-rayed) hospital personnel will check the identity of the patient by scanning the patient identification band barcode 1 and will check the procedure by scanning the bar code associated with the procedure. The portable computer means 3 will check the physician instruction file 6 to verify the procedure was ordered by a physician. If the procedure was ordered for the patient, the portable computer means will display the message "verified". If an error occurs in this process, an appropriate error message will be displayed by the portable computer means.

The communication link means 10 between the portable computer means 3 and the host computer means 7 may be by direct wire, phone modem, radio, infrared or other communication link means.

Figure 2:
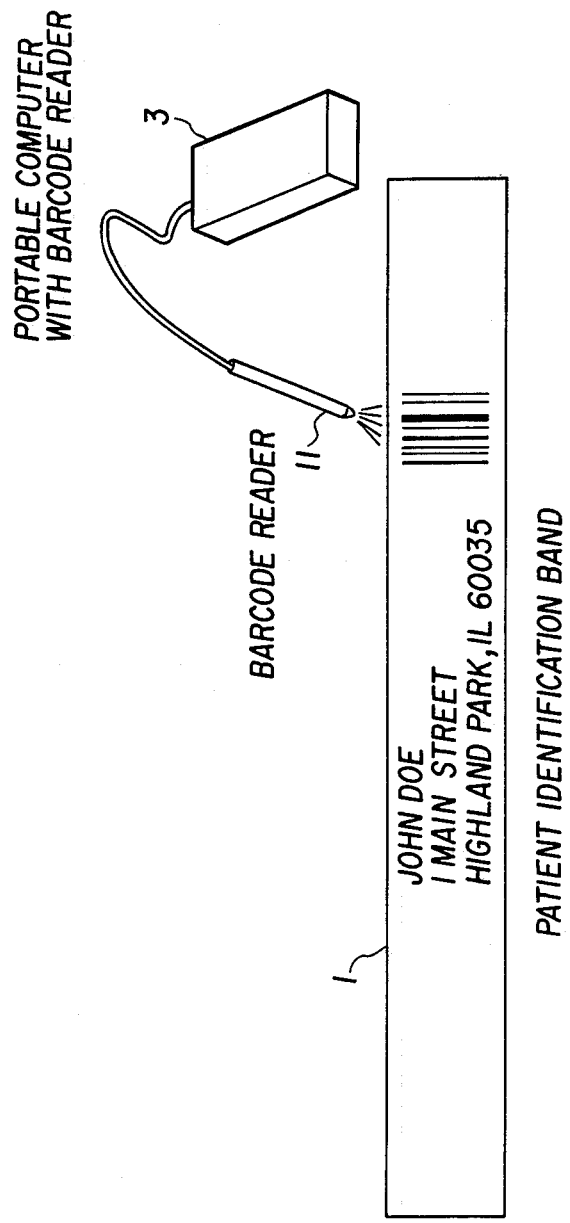
FIG. 2 discloses the preferred machine-readable code of the invention.

FIG. 2 shows a patient identification band with barcode 1. The barcode may be of any standard design but should be the same as the standard used by drug manufacturers. The barcode reader 11 scans the patient identification band to record the patient identity in the transaction file 5 shown in FIG. 1.

I claim:

1. A hospital error limiting system employing bar codes for identifying patients, medications, goods, services and procedures comprising:

host computer means for maintaining a patient history file, which indicates when particular medications, goods, services or procedures were delivered to a particular patient in the past, and a physician instruction file, which indicate what particular medications, goods, services or procedures are to be given to a particular patient at a particular time interval.

communication link means to link said host computer means to a portable computer means for transferring said patient history file and said physician instruction file between said host computer means and said portable computer means.

wherein said portable computer means comprises a portable memory means for storing said patient history file and said physician instruction file, portable bar code reading means for identifying a patient by reading a bar code provided to said patient, and for identifying medications, good, services or procedures proposed to be delivered to said patient, by reading a bar code provided on said medications, goods, services or procedures, portable processing means for processing the bar codes read by said portable bar code reading means so as to determine if said identified medications, goods, services or procedures are permitted to be delivered to said identified patient, according to said patient history file and said physician instruction file in said portable memory means, and for updating said patient history file in said portable memory means if said identified medications, goods, services or procedures are permitted to be delivered to said identified patient, wherein said determination requires that said identified medications, goods, services or procedures are related to said identified patient in said physician instruction file in the portable memory means and that said identified medications, goods, services or procedures would be delivered to said identified patient at an appropriate time according to when identified medications, goods, services or procedures were lasts delivered to the identified patient in the past as indicated in the patient history file in the portable memory means and according to the time interval in said physician instruction file in said portable memory means to grant permission to deliver said identified medications, goods, services or procedures, and portable display means for indicating the determination of said portable processing means, Wherein said patient history file in said host computer means is updated periodically by transferring said updated patient history file in said portable computer means to said host computer means via said communication link means.

* * * * *